United States Patent [19]

Hasson

[11] Patent Number: 5,201,742
[45] Date of Patent: Apr. 13, 1993

[54] SUPPORT JIG FOR A SURGICAL INSTRUMENT

[76] Inventor: Harrith M. Hasson, 2043 N. Sedgwick, Chicago, Ill. 60614

[21] Appl. No.: 686,149

[22] Filed: Apr. 16, 1991

[51] Int. Cl.⁵ .................. A61B 19/00; A61B 17/00
[52] U.S. Cl. .................................. 606/130; 606/1; 606/108
[58] Field of Search .............. 606/53, 54, 55, 56, 606/130, 1, 108

[56] References Cited

U.S. PATENT DOCUMENTS

| 2,697,433 | 12/1954 | Zehnder | 606/130 |
| 3,021,842 | 2/1962 | Flood | 606/130 |
| 3,115,140 | 12/1963 | Volkman | 606/130 |
| 4,592,352 | 6/1986 | Patil | 606/130 |
| 4,608,977 | 9/1986 | Brown | 606/130 |
| 4,706,665 | 11/1987 | Gouda | 606/130 |
| 4,841,967 | 6/1989 | Chang et al. | 606/130 |
| 4,883,053 | 11/1989 | Simon | 606/130 |
| 5,002,557 | 3/1991 | Masson | 606/191 |
| 5,030,223 | 7/1991 | Anderson et al. | 606/130 |
| 5,100,411 | 3/1992 | Koutrouvelis | 606/130 |

FOREIGN PATENT DOCUMENTS 0818711  8/1959  United Kingdom ............ 606/130

Primary Examiner—Stephen C. Pellegrino
Assistant Examiner—Glenn Dawson
Attorney, Agent, or Firm—Wood, Phillips, VanSanten, Hoffman & Ertel

[57] ABSTRACT

A jig for consistently orienting surgical instrument. The jig has a base for placement against a tissue in the vicinity of where a surgical procedure is to be performed, a yoke, an instrument support sleeve on the yoke and defining a passageway for the introduction of a surgical instrument to be inserted into the tissue, structure for supporting the yoke on the base for movement relative to the base, and structure for maintaining the yoke in a plurality of selected positions relative to the base.

21 Claims, 3 Drawing Sheets

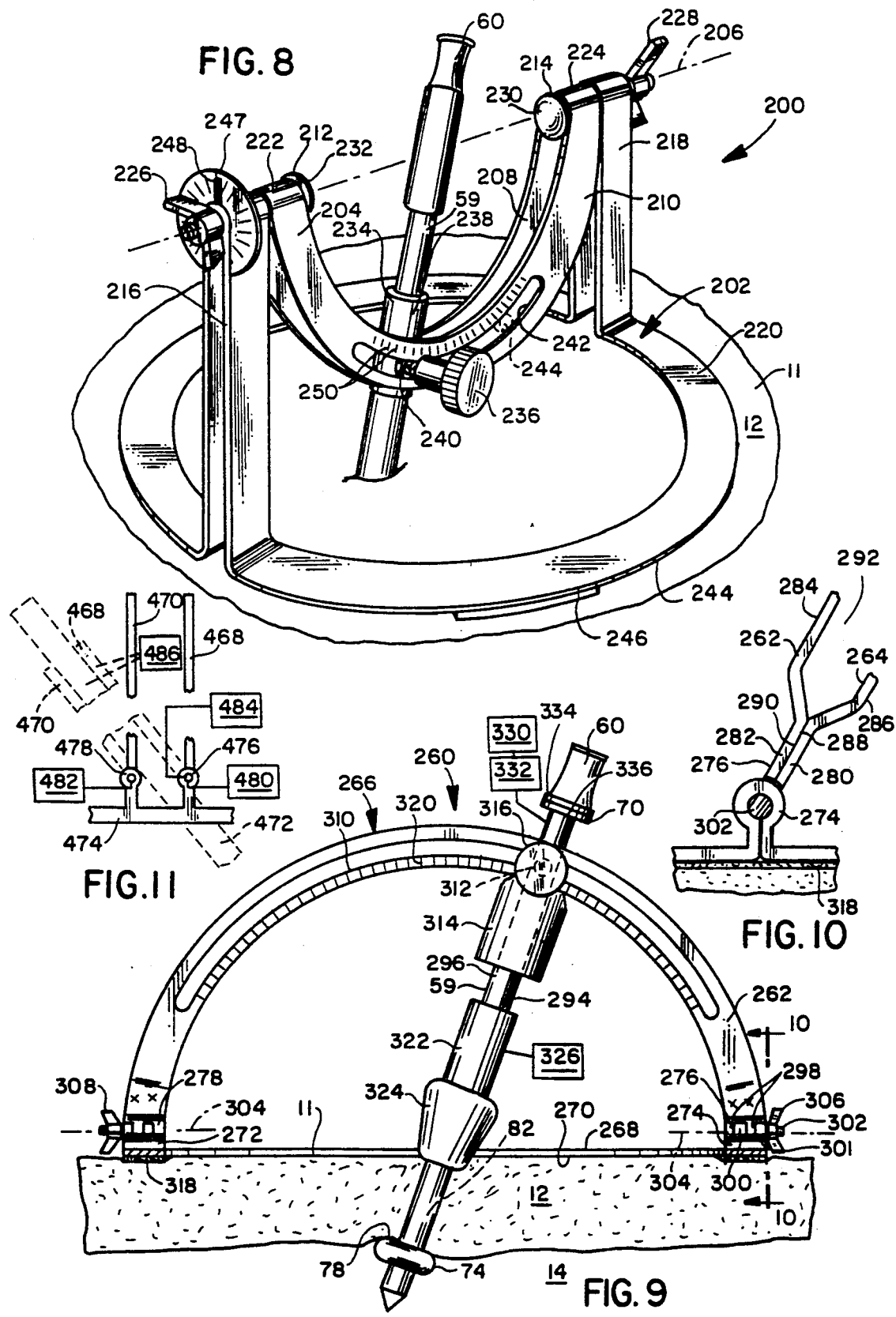

SUPPORT JIG FOR A SURGICAL INSTRUMENT

BACKGROUND OF THE INVENTION

1. Field of the Invention

This invention relates to surgical procedures, such as laparoscopy, and, more particularly, to a jig for consistently guiding introduction of laparoscopic surgical instruments through a tissue in any of a number of preselected orientations.

2. Background Art

Laparoscopic surgery is a widely accepted alternative to conventional surgery. A principal advantage of laparoscopic surgery is that it generally requires only small incisions in the body tissue, thereby permitting the performance of many major surgical operations on an out-patient basis.

The inventor herein has obtained numerous U.S. patents covering instruments particularly adaptable for use in laparoscopic surgery. Among these are U.S. Pat. No. 4,935,006, entitled "Suction and Irrigation Device" and U.S. Pat. No. 4,944,741, entitled "Laparoscopic Instrument With Pivotable Support Arm".

It should be understood that laparoscopy, as used throughout this specification, is intended in a generic sense to include other surgical procedures, such as endoscopy, etc. which, from a mechanical standpoint, are performed in a similar manner.

The basic laparoscopic instrument consists of an elongate, hollow sleeve with proximal and distal ends, the latter of which is directed through body tissue and into a cavity in which the surgical procedure is to be performed. To facilitate insertion, a spike/trocar is directed through the sleeve and, when fully inserted therein, has a protruding, sharpened point at the distal sleeve end. After a small incision is made in the tissue, the sleeve, with the spike/trocar directed fully thereinto, is forced through the incision.

The inventor herein has devised structure for holding the sleeve in a relatively stable position with respect to tissue through which it extends to thereby facilitate instrument removal and introduction without disturbing the alignment of the sleeve. One such structure is shown in U.S. patent application Ser. No. 334,452, entitled "Laparoscopic Cannula". That device has a sleeve and a membrane thereon which is expandable once the distal end is projected into the body cavity and a slidable collar on the sleeve which, in conjunction with the membrane, positively captures the tissue wall. The collar has a tapered surface which depresses the tissue around the sleeve to provide a relatively airtight seal around the incision. This seal is required to maintain in the cavity $CO_2$ gas or other gas that may be utilized to distend the cavity to facilitate performance of the surgical procedure. The tapered surface on the collar permits the angle of the sleeve axis to be changed with respect to the tissue without compromising the seal.

One problem with the above described device is that, while the sleeve is positively held in place on the tissue and the integrity of the seal maintained throughout a range of movement of the sleeve, that structure does not permit the sleeve to be selectively reoriented and maintained in the reoriented state. For example, if the sleeve is introduced at one location through the abdominal wall, the curvature of the abdominal wall, when distended, will naturally hold the sleeve in a first orientation. While the sleeve may be manually reoriented by the surgeon, the sleeve naturally tends back towards a centered position. It is difficult, if not impossible, for the surgeon to access a different area in the body cavity, and maintain that position of the sleeve, as to insert different instruments. As a result, it may instead be necessary to provide a separate incision, which is obviously undesirable if the second site is accessible through the first incision.

A further problem with the above system is that, regardless of how securely the sleeve is held relative to the tissue wall, the sleeve tends to float freely around the incision site due to the fact that the tissue wall itself is flexible. Upon the introduction of the instrument, the surgeon may be required to search each time for the exact location at which the operation is being performed.

SUMMARY OF THE INVENTION

The present invention is specifically directed to overcoming the above enumerated problems in a novel and simple manner.

The present invention is directed to a jig for consistently maintaining a surgical instrument in a predetermined orientation relative to a subjacent tissue on which the jig is supported. The jig consists of a base for placement against the tissue in the vicinity of where the surgical procedure is to be performed, an instrument support member, and cooperating structure on the base and instrument support member for maintaining the instrument support member in a predetermined position relative to the base and a subjacent tissue on which the jig is supported.

The present invention allows the surgeon to pre-position the jig, after which different instruments can be directed consistently to the same location in the body cavity. This avoids the surgeons' having to search for the exact site of the surgery each time a new instrument is introduced. At the same time, the jig stabilizes the position of the instrument associated therewith.

In a preferred form, the cooperating structure on the base and the instrument support member is used to selectively maintain the instrument support member in a plurality of different positions relative to the base.

It is possible with the inventive structure for the surgeon to adjust the location of the instrument and, once this is achieved, to lock the jig in an orientation which fixes the desired position of the instrument.

Preferably, the instrument support member has a sleeve defining a passageway for the introduction of a surgical instrument.

In a preferred form, the cooperating structure on the instrument support member and base is a concave surface on one of the base and instrument support member and a convex surface on the other of the base and instrument support member, which surfaces cooperate with each other to guide universal relative movement between the instrument support member and base. Preferably, the instrument support member has a spherical configuration defining a convex surface and the base has a socket for reception of the instrument support member and defines a concave surface.

In one form of the invention, the instrument support member defines a sleeve and is defined at least in part by first and second removably separable parts. With the first and second parts separated, placement of the surgical instrument in its operative position is facilitated.

In a preferred form, there is locking structure for fixing the positions of both the instrument support member relative to the base and the sleeve/instrument relative to the instrument support member.

Preferably, the base has a flat wall surface for placement directly against the subjacent tissue. In one form, the socket for the spherically-shaped instrument support member is spaced from the plane of the flat annular wall surface of the base.

In one form of the invention, the base has a curved yoke and the cooperating structure on the base and instrument support member is a pin and slot connection. Preferably, the yoke has a curved slot and the instrument support member has a guide element, such as a pin, that is guided in an arcuate path in the curved yoke slot. The pin can be locked in a desired position relative to the yoke to thereby fix the relative positions of the yoke and instrument support member. The yoke is preferably U-shaped and may open upwardly or downwardly.

In one form of the invention, the base has a first wall with a flat surface for placement against a subjacent tissue and a second wall mounted to the first wall for pivoting movement relative to the first wall about an axis that is transverse to the plane of the first flat wall surface. In a preferred form, there are structures for selectively locking the first and second walls against relative movement. The yoke is preferably attached to one of the walls.

To add rigidity to the underlying tissue and to prevent shifting of the jig, the jig base is preferably releasably adhered to the subjacent tissue as by an adhesive pad.

The invention also contemplates a jig consisting of a base for placement against a tissue in the vicinity of where a surgical procedure is to be performed, a yoke, an instrument support member on the yoke and defining a passageway for the introduction of a surgical instrument to be extended into the tissue, structure for supporting the yoke on the base for movement relative to the base, and structure for maintaining the yoke in a plurality of selected positions relative to the base.

In a preferred form, the instrument support member is mounted to the yoke for movement relative thereto while the yoke is in turn pivotably connected to the base for rotation about an axis.

Structure is provided for captively embracing a tissue through which the sleeve is extended. In a preferred form, the instrument support member defines a sleeve having proximal and distal ends and the cooperating structure for embracing the tissue is an expandable member which is positionable selectively in expanded and collapsed states at a distal end of the sleeve and a collar mounted to the sleeve for sliding movement selectively towards and away from the expandable member. With the expandable member in its collapsed state, the sleeve can be directed through an incision in a tissue after which the expandable member can be placed in its expanded state and the collar slid along the sleeve to captively embrace the tissue in conjunction with the expandable member.

In one form, the yoke consists of cooperating, U-shaped elements, each with spaced free ends, and a base, with the free ends of the elements pivotably attached to the base so that the ends of the U-shaped elements are in adjacent relationship on the base and so that the U-shaped elements are pivotable selectively towards and away from each other.

In one form, at least one of the U-shaped elements is biased towards the other to captively engage the instrument support member, which preferably can be fixed with respect to at least one of the U-shaped elements.

The pivot axes for the U-shaped elements may be either coincident or in parallel and spaced relationship.

BRIEF DESCRIPTION OF THE DRAWINGS

FIG. 8 is a perspective view of a further modified form of jig for holding a surgical instrument according to the present invention and having a surgical instrument operatively associated therewith and extending through a subjacent tissue;

FIG. 9 is a cross-sectional view of a still further modified form of jig according to the present invention operatively associated with a surgical instrument extending through underlying tissue;

FIG. 10 is an enlarged cross-sectional view of the connection between a movable yoke and base taken along line 10—10 of FIG. 9; and FIG. 11 is a view similar to that in FIG. 10 and showing a modified form of connection between the yoke and base.

DETAILED DESCRIPTION OF THE DRAWINGS

Figure 1:
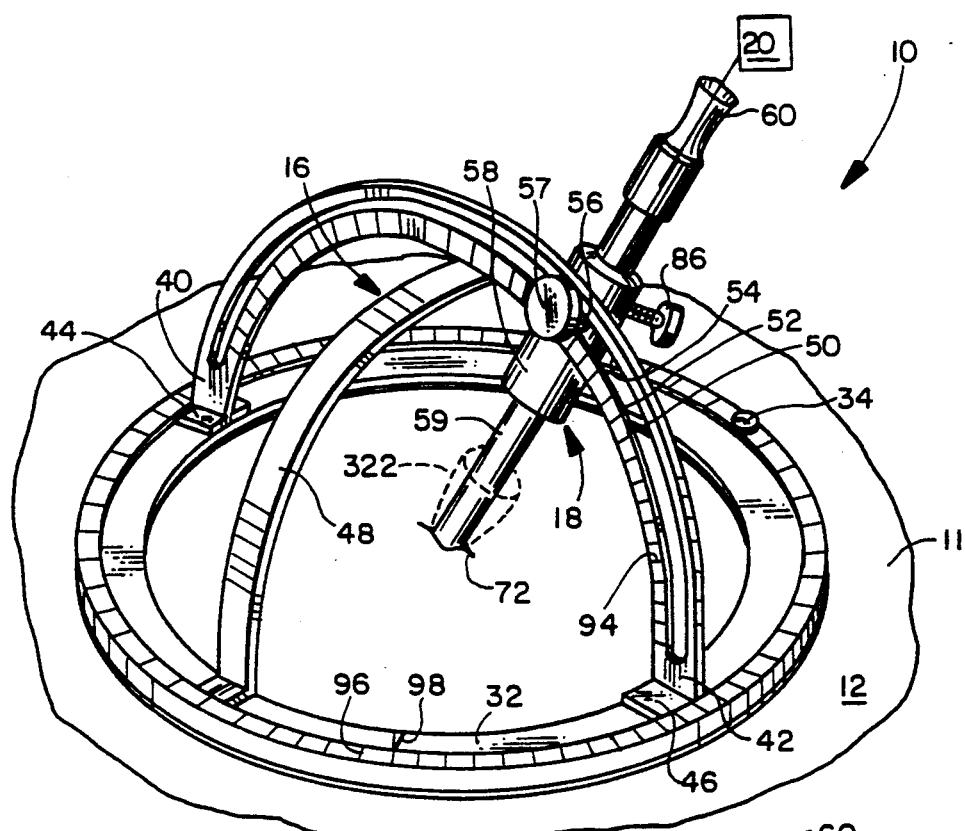
FIG. 1 is a perspective view of a jig for holding a surgical instrument according to the present invention and showing a surgical instrument operatively associated therewith and extending through the tissue on which the jig is supported.
Figure 2:
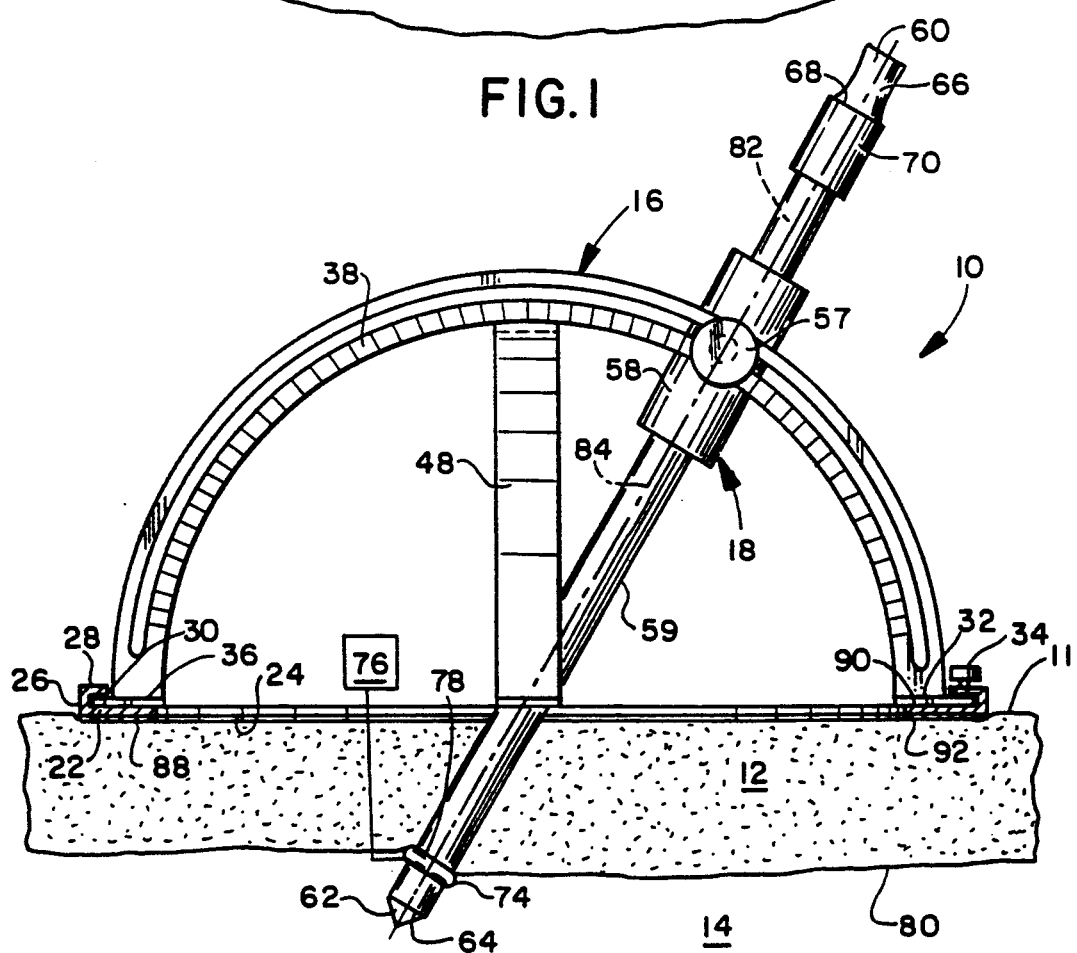
FIG. 2 is a cross-sectional view of the jig and tissue of FIG. 1.
Figure 3:
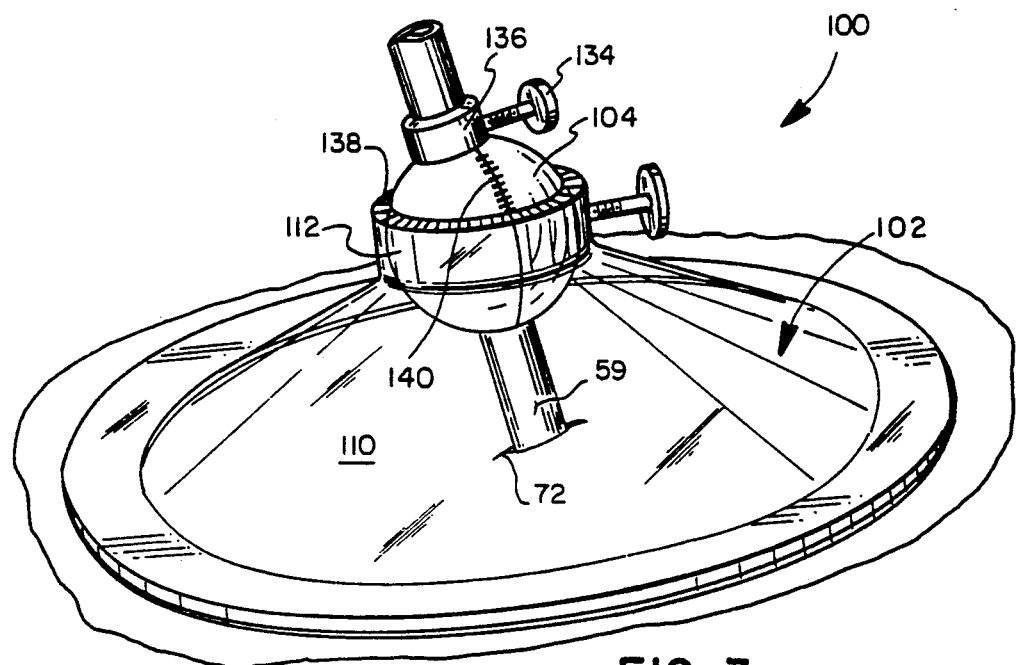
FIG. 3 is a perspective view of a modified form of jig according to the present invention with a surgical instrument operatively associated therewith and extending through an underlying tissue.
Figure 4:
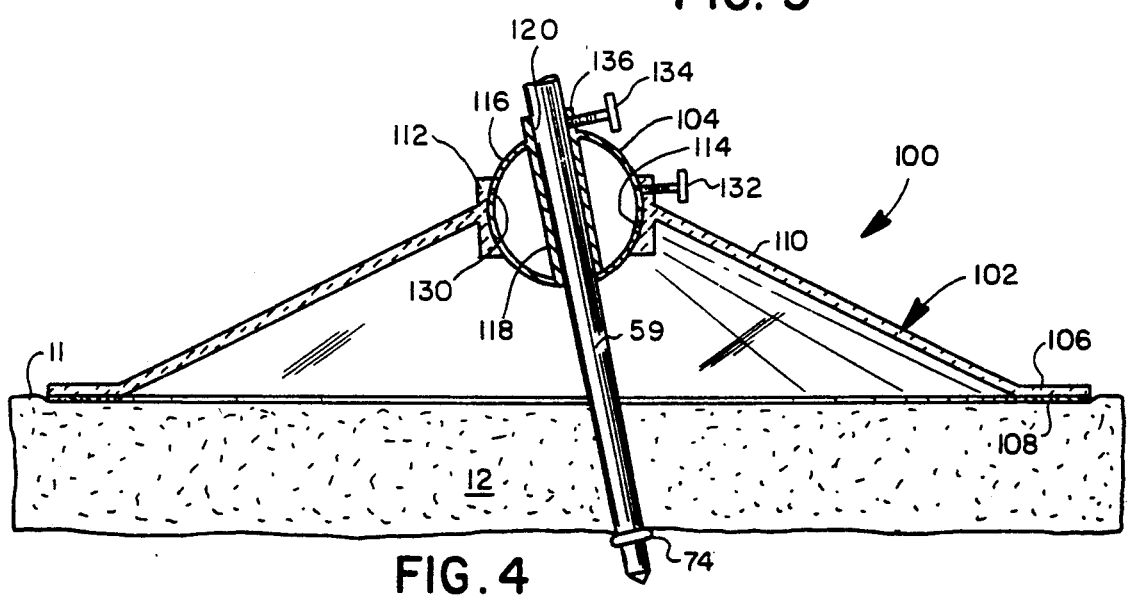
FIG. 4 is a cross-sectional view of the jig and tissue of FIG. 3.
Figure 6:
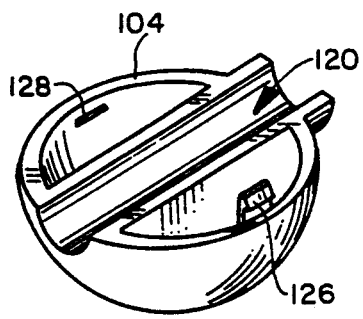
FIG. 6 is a perspective view of one of two joinable halves defining the instrument support member of FIG. 5.
Figure 5:
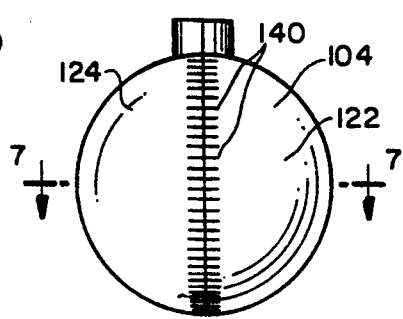
FIG. 5 is a side elevation view of an instrument support member on the jig of FIGS. 3 and 4.
Figure 7:
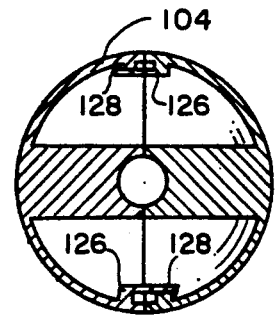
FIG. 7 is a cross-sectional view of the instrument support member taken along line 7—7 of FIG. 5.

In FIGS. 1 and 2, a preferred form of surgical jig, according to the present invention, is shown at 10. The surgical jig 10 is designed to be supported on the outer surface 11 of underlying tissue 12, which bounds a body cavity 14 within which a surgical procedure is to be performed. The jig 10 consists of a base 16 on which an instrument support member 18 is mounted. The instrument support member 18 holds an instrument 20, shown schematically in FIG. 1. A wide range of different types of instruments 20 can be used to perform different laparoscopic procedures. A precise description of these instruments 20 is unnecessary to understand the present invention and is, therefore, omitted herefrom.

The base 16 has a first wall/wall part 22, which is annular and defines a flat, downwardly facing surface 24 to facially engage the tissue outer surface 11. The wall 22 has an upturned annular end 26 and a returned, annular bend 28 which, in conjunction with the end 26, defines a receptacle 30 for a second, annular base wall/wall part 32. The walls 22, 32, so engaged, define a turntable arrangement to allow relative pivoting movement between the first and second walls 22, 32 about a vertical axis. A set screw 34 is directed through the bend 28 and against the upper surface 36 of the second wall 32 to fix the relative positions of the first and second walls 22, 32, respectively, as desired.

An inverted, U-shaped yoke 38 spans between diametrically opposite locations on the second wall 32 and has opposite ends 40, 42 connected to the wall 32 through mounting pads 44, 46, respectively. A curved brace 48 connects between the mid portion of the yoke 38 and the second wall 32 to reinforce the yoke 38 in its upstanding position of FIGS. 1 and 2.

The yoke 38 has an arcuate slot 50 extending through approximately 180°. The edges 52, 54 bounding the slot 50 guide movement of a pin 56 on the instrument support member 18. The pin 56 is threaded and has an enlarged, knurled head 57 to facilitate its operation. The pin 56 extends through the slot 50 from one side of the yoke 38 and into a threaded bore in an enlarged, cylindrical body 58 on the instrument support member 18 on the other side of the yoke.

With the above arrangement, the instrument support member 18 can be reoriented relative to the underlying tissue 12 by sliding the pin 56 lengthwise along the slot 50 and/or rotating the second wall 32 relative to the first wall 22.

To better understand the importance of the surgical jig 10, a short summary of laparoscopic procedures is in order. In a typical laparoscopic procedure, an elongate sleeve 59 is directed through tissue 12 to provide a working passageway into the cavity 14. The sleeve 59 is inserted by first directing a spike/trocar 60 downwardly through the sleeve 59 so that a sharpened end 62 on the spike/trocar 60 projects from the bottom free edge 64 of the sleeve 59. The spike/trocar 60 has an enlarged head 66 which abuts a shoulder 68 on an enlargement 70 on the sleeve 59 in its fully extended position.

A small incision 72 is made in the tissue 12 to accept the sleeve 59. With the spike/trocar 60 in the position of FIGS. 1 and 2, the sleeve 59 and trocar 60 are forced through the incision 72 until the sleeve free edge 64 projects into the cavity 14. The spike/trocar 60, which wedges the tissue 12 out around the incision 72 to facilitate insertion of the sleeve 59, can then be removed from the sleeve 59.

To prevent inadvertent withdrawal of the sleeve 59 from its operative position in FIGS. 1 and 2, the lower sleeve end is provided with an inflatable membrane 74, which can be selectively inflated and deflated through a pump mechanism, shown schematically at 76 in FIG. 2. As can be seen in FIG. 2, the membrane 74 defines an annular shoulder 78 which abuts an inwardly facing tissue surface 80 to block withdrawal of the sleeve 59. The membrane 74 also seals the incision 72 to prevent the escape of a gas which is used to distend the cavity 14 to facilitate performance of the surgical procedure.

With the spike/trocar 60 removed from the sleeve 59, an unobstructed passageway 82 is defined by the sleeve 59. Any desired instrument 20 can be directed downwardly through the internal passageway 82 defined by the sleeve 59 into the cavity 14. By loosening the set screw 34 and pin 56, the instrument support member 18 can be repositioned to place the axis 84 of the sleeve 59 in line with the area to be operated upon. Once the desired orientation for the sleeve 59 is selected, the pin 56 is tightened through manipulation of the enlarged head 57 thereon and in similar fashion the set screw 34 is turned to secure the walls 22, 32 against relative rotation.

To positively seal the incision 72 with the sleeve 59 in its desired orientation, the sleeve 59 is drawn upwardly relative to the instrument support member 18 to bear the membrane 74 sealingly against the inside surface 80 of the tissue 12. Once this is done, a set screw 86 is tightened to prevent relative lengthwise shifting between the instrument support member 18 and the sleeve 59.

The jig 10 is rigidly held on the tissue 12 because of the substantial contact area between the jig surface 24 and the tissue surface 11. To add further stability to the jig 10, a pad 88 is provided on the wall 24 and has an adhesive layer on its opposite faces 90, 92 to bond the pad 88 to both the wall 22 and the tissue 12. This rigidifies the tissue 12 under the jig 10 and prevents inadvertent shifting of the jig 10 relative to the tissue 12.

To add further versatility to the jig 10, graduations 94 are provided on the yoke 38 to allow relocation of the support member 18 in a desired position after it has been moved. Similar graduations 96 are provided on the wall 22 and are alignable with an indicating arrow 98 to allow resetting of a selected relative position between the walls 22, 32.

A modified form of jig is shown at 100 in FIGS. 3-7. The jig 100, as the jig 10 in the prior embodiment, has a base 102 and an instrument supporting member 104. The base 102 has an annular wall 106 for bearing on the underlying tissue 12. An optional adhesive pad 108 is interposed between the wall 106 and the tissue outer surface 11.

A conical skirt 110 projects upwardly from the wall 106 and terminates at a block 112. The block 112, which has a spherical, annular surface 114, defines a socket for the instrument support member 104.

The instrument support member 104 has a generally spherical configuration and an outer surface 116 which nests against the concave surface 114 to provide a ball and socket connection. The instrument support member 104 is thereby universally movable relative to the base 102.

The instrument support member 104 defines an internal sleeve 118 in turn defining a passageway 120 for the sleeve 59, described earlier with respect to the embodiment in FIGS. 1 and 2.

To facilitate placement of the sleeve 59 in the passageway 120, the instrument support member 104 is defined by two separably joinable halves 122, 124. The support member halves 122, 124 are preferably snap-fit into the operative position of FIGS. 3-5. To accomplish this, deflectable tabs 126 are provided, one each on its halves 22, 24, to engage behind shoulders 128, at diametrically opposite locations on the support member 104.

The combination of the sleeve 59 and support member 104 can be preassembled and dropped through the opening 130 in the block 112. The support member 104 and block 112 can be relatively dimensioned to allow the support member 104 to be snap fit into its operative position. A set screw 132 extends through the block 112 above vertical center and against the outer surface 116 of the support member 104 to fix the location of the support member 104 relative to the block 112 with the sleeve 59 in a desired orientation.

A separate set screw 134 extends through an annular extension 136 on the sleeve 118 on the support member 104 to bear against the sleeve 59 to thereby prevent relative lengthwise shifting between the sleeve 59 and support member 104. The sleeve 59, once in its desired orientation, is drawn upwardly to bear the membrane 74 against the tissue 12, whereupon the set screw 134 is tightened to secure the connection.

The jig 100, as the previously described jig 10, permits a wide range of adjustment for the orientation of the sleeve 59. A turntable arrangement could optionally be provided on the wall 106, such as in the embodiment shown in FIGS. 1 and 2, to add versatility to the jig 100. Graduations 138, 140 are provided on the support member 104 and base 102 to facilitate resetting of the support member 104 and base 102 in a desired relative position.

A further modified form of jig is shown in FIG. 8 at 200. The jig 200 consists of a base 202, a yoke 204 mounted for movement relative to the base 202, and a sleeve 59, as in the prior embodiments, through which an instrument can be passed.

The yoke 204 is supported on the base 202 for pivoting movement relative thereto about a horizontal axis 206. The yoke 204 is generally U-shaped and defined by a single shaped piece of metal which is folded against itself to provide a double thickness with first and second U-shaped, spaced walls 208, 210.

Pivot guide bolts 212, 214 are carried on two upright supports 216, 218, projecting upwardly at diametrically opposite locations from the ring-shaped bottom wall 220 of the base 202. The bolts 212, 214 cooperatively define a cradle for the downwardly opening yoke ends 222, 224, respectively. Wing nuts 226, 228 are provided on the bolts 212, 214 and, when tightened, fix and maintain the position of the yoke 204 on the base 202. Tightening of the wing nut 228 squeezes the yoke end 224 between an enlarged head 230 on the bolt 214 and the support 218. Similarly, tightening of the wing nut 226 draws an enlarged head 232 on the bolt 212 frictionally against the support 216. By simply loosening the wing nut 226, 228, the yoke 204 can be freed to pivot about its axis 206.

The sleeve 59 is held to the yoke 204 through a connector 234, through which the sleeve 59 is extended. The position of the connector 234 can be fixed relative to the sleeve 59 by a set screw 236. The connector 234 has a body 238 which is closely received between the yoke walls 208, 210. A guide element 240 on the connector 234 projects outwardly through an arcuate slot 242 in the yoke wall 210. An optional guide element (not shown) can be provided to cooperate with a similar slot (not shown) on the opposite yoke wall 208. The description herein is limited to exemplary cooperating guide element 240 and slot 242.

The guide element 240 is shown to have a square/rectangular cross section to be keyed to the slot 242. This prohibits pivoting of the sleeve 59 about an axis extending at right angles to the lengthwise extent of the sleeve 59. Once the position for the sleeve 59 is selected, the set screw 236 can be tightened to draw the wall 210 against the connector body 238 so that the connector 234 is frictionally maintained against relative movement to the yoke 204.

Alternatively, a cylindrical guide element 244 can be employed in place of the guide element 240 on the connector 234. The guide element 240 is free to pivot about its axis to add an additional degree of freedom of movement of the sleeve 59 relative to the yoke 240. This enhances the versatility of the jig 200.

It can be seen that, with the above structure, the lengthwise axis of the sleeve 59 can be substantially universally oriented with respect to the underlying tissue 12. Tightening of the wing nuts 226, 228 and set screw 236 permits fixing of the sleeve 59 in any desired orientation.

The base wall 220 has a substantially flat underside surface 244 which facially engages the exposed outer surface 11 of the tissue 12. The base wall 220 can take any configuration, however, the annular configuration shown or a circular disk shape is preferred for stability. The important thing is to have sufficient contact areas established between the underside surface 244 of the base 202 so that the jig 200 is not inclined to tip. In a preferred form, the diameter of the base 202, as well as the corresponding elements in the prior embodiments, is on the order of 2-5 inches. In a preferred form, an adhesive layer 246 is provided on the surface 244 to releasably adhere the base 202 to the underlying tissue 12, as in the prior embodiments.

To facilitate re-setting of the jig 200, a graduated disk 247 is provided on the support 216 to cooperate with an indicating needle 248 that rotates with the yoke 204. Graduations 250 are also provided on the yoke 204 to consistently determine the location of the connector 234 relative to the yoke 204.

The jig 200 can be set up in several different ways. For example, the sleeve 59, yoke 204 and base 202 can be preassembled. To effect insertion of the sleeve 59 through the tissue 12, the entire jig 200 is moved as a unit against the tissue 12.

As an alternative to the above procedure, the yoke 204 and sleeve 59 can be removed from the base 202. The base can be set in position on the tissue 12 after which the yoke 204, with the sleeve 59 thereon, is placed on the bolts 212, 214 to straddle the same. The enlarged bolt heads 230, 232 can be made rectangular in shape so as to be slidable between the walls 208, 210 or, alternatively, the walls 208, 210 can be slightly spread to be extended over the bolt heads 230, 232.

A further alternative manner of setting up the jig 200 is to remove the set screw 236 and remove the sleeve 59 from the yoke 204. The base 202 and yoke 204 can then be prepositioned, after which the sleeve 59 is directed downwardly through the tissue 12 and attached to the yoke 204.

In FIGS. 9 and 10, a still further modified form of jig, according to the present invention, is shown at 260. The jig 260 employs two U-shaped elements 262, 264, which cooperatively define a U-shaped, downwardly opening yoke 266.

The jig 260 has a base 268 having a tissue engaging bottom surface 270 similar in size and configuration to the bottom surface 244 on the jig 200. The base 168 has spaced supports 272, 274 for pivotably mounting the free end 276, 278 of the U-shaped element 262 and the free ends 280 (one shown) of the U-shaped element 264. The relationship between the elements 262, 264 and supports 272, 274 will be described with respect to exemplary support 274 in FIGS. 9 and 10. The connection of the other support 272 is similar.

The free end 282 of the U-shaped element 262 is offset from the flat body 284 thereon. The end 280 is similarly offset from the body 286 of the element 264. With the flat surface 288 on the free end 282 and the surface 290 on the end 280 facially engaged, the offset end arrangement on the elements 262, 264 results in a space 292 being defined between the bodies 284, 286 of the elements 262, 264, respectively, having a width approximately equal to the diameter of the outer surface 294 of the body 296 of the sleeve 59.

The element 262 has knuckles 298 meshed with a knuckle 300 on the element 264 on the base 268 and a knuckle 301 on the element 264. A pivot bolt 302 extends through the meshed knuckles 298, 300, 301 to guide relative pivoting movement of the elements 262, 264 about a horizontal axis 304. By tightening the wing nuts 306, 308, the yoke 266 can be maintained in any desired position within its range of movement.

The element 262 has a guide slot 310 for a guide element 312 on a housing 314 which supports the sleeve 59. A set screw 316 on the housing 314 simultaneously maintains the desired positions of the sleeve 59 relative to the element 262. As in the embodiment in FIG. 8, a corresponding slot (not shown) could be provided on the element 264 for a guide element (not shown) located diametrically opposite to the guide element 312.

An adhesive layer 318 shown on the bottom of the base 268, as in prior embodiments. Graduations 320 are also provided on the element 262 to facilitate relocation of the sleeve 59 in a desired position.

FIG. 9 shows a slightly modified form of support structure associated with the sleeve 59. In FIG. 9, a slidable collar 322 is provided with a conical surface 324 which is pressed against the tissue 12 so that the tissue 12 is positively captured between the conical surface 324 and shoulder 78 on the membrane 74. A locking mechanism at 326 fixes the collar 322 relative to the sleeve 59 to assure that the leakproof seal is maintained around the incision 72. The collar 322 is optionally used on the jig 10 in FIGS. 1 and 2. However, the seal in most instances around the incision 72 can be maintained by the membrane 74 alone.

A pressurized supply of gas 330 is used to distend the cavity 14 bounded by the tissue 12. Gas from the supply 330 is delivered into the sleeve passageway 82 through a one way valve 332 into the cavity 14. A gasket 334 seals the outer end 336 of the sleeve 59 to prevent the escape of gas introduced into the cavity 14.

A further modified form of the invention is shown in FIG. 11. The structure in FIG. 11 has inverted U-shaped elements 468, 470 between which a sleeve 472 is received. The elements 468, 470 are mounted on a base 474 for pivoting movement about supports 476, 478 extending upwardly from the base 474. Biasing structure 480 is provided to urge the element 468 towards the other element 470 and similar biasing structure 482 urges element 470 towards element 468. There is a resulting compressive force between the elements 468, 470 on the sleeve 472 at all times throughout the range of movement of the elements 468, 470.

Because of the parallel and spaced arrangement of the pivot axes for the elements 468, 470, the elements 468, 470 and sleeve 472 do not rotate as a unit. That is, as the sleeve 472 pivots from the solid line position in FIG. 4 in a counterclockwise direction towards the phantom line position, the element 468 slides down the sleeve 472 and the element 470 slides up the sleeve 472.

By fixing either element 468, 470 relative to the base 474, as by the use of a conventional locking means 484, the sleeve 472 is fixed. The biasing structure 480, 482 can be made sufficiently strong to produce a captive force on the sleeve 472 that prevents free sliding of the sleeve 472 parallel to the planar surfaces on the elements 468, 470. The sleeve 472 can further be held fixedly by holding either of the elements 468, 470 against shifting lengthwise of the sleeve 472, as by structure known to those skilled in the art and indicated schematically at 486.

The foregoing disclosure of specific embodiments is intended to be illustrative of the broad concepts comprehended by the invention.

I claim:

1. A jig for consistently maintaining a surgical instrument in a predetermined orientation relative to a subjacent tissue on which the jig is supported, said jig comprising:

a base having a flat surface residing in a first plane for placement in facially engaged relationship with a tissue in the vicinity of where a surgical procedure is to be performed;

an instrument support member;

cooperating means on the base and instrument support member for maintaining the instrument support member in a predetermined position relative to the base and a subjacent tissue on which the jig is supported, wherein the cooperating means comprises a concave surface on one of the base and instrument support member and a convex surface on the other of the base and instrument support member, said concave and convex surfaces cooperating with each other to guide universal relative movement between the instrument support member and base; and means for releasably fixing the convex and concave surfaces in a plurality of different positions relative to each other, said convex and concave surfaces being fully spaced from the first plane, whereby the jig can be used to positively maintain a surgical instrument in a desired orientation relative to a subjacent tissue to thereby facilitate the performance of surgical procedures;

wherein the instrument support member has a spherical configuration defining the convex surface and the base has a socket for reception of the instrument support member and defines the concave surface.

2. A jig for consistently maintaining a surgical instrument in a predetermined orientation relative to a subjacent tissue on which the jig is supported, said jig comprising:

a base for placement against a tissue in the vicinity of where a surgical procedure is to be performed;

an instrument support member; and cooperating means on the base and instrument support member for maintaining the instrument support member in a predetermined position relative to the base and a subjacent tissue on which the jig is supported, whereby the jig can be used to positively maintain a surgical instrument in a desired orientation relative to a subjacent tissue to thereby facilitate the performance of surgical procedures, wherein the cooperating means comprises means for selectively maintaining the instrument support member in a plurality of different positions relative to the base, wherein the cooperating means comprises a concave surface on one of the base and instrument support member and a convex surface on the other of the base and instrument support member, said concave and convex surfaces cooperating with each other to guide universal relative movement between the instrument support member and base, wherein the instrument support member has a spherical configuration defining the convex surface and the base has a socket for reception of the instrument support member and defines the concave surface, wherein the instrument support member has sleeve defining a passageway for the introduction of a surgical instrument to be extended into a subjacent tissue on which the jig is supported and the instrument support member has first and second separable parts which when separated facilitate placement of a surgical instrument in the sleeve passageway, said first and second separable parts cooperatively defining at least a part of said convex surface.

3. A jig for consistently maintaining a surgical instrument in a predetermined orientation relative to a subjacent tissue on which the jig is supported, said jig comprising:

a base for placement against a tissue in the vicinity of where a surgical procedure is to be performed;

an instrument support member; and cooperating means on the base and instrument support member for maintaining the instrument support member in a predetermined position relative to the base and a subjacent tissue on which the jig is supported, whereby the jig can be used to positively maintain a surgical instrument in a desired orientation relative to a subjacent tissue to thereby facilitate the performance of surgical procedures, wherein the cooperating means comprises means for selectively maintaining the instrument support member in a plurality of different positions relative to the base, wherein the cooperating means comprises a concave surface on one of the base and instrument support member and a convex surface on the other of the base and instrument support member, said concave and convex surfaces cooperating with each other to guide universal relative movement between the instrument support member and base, wherein the instrument support member has a spherical configuration defining the convex surface and the base has a socket for reception of the instrument support member and defines the concave surface, wherein the cooperating means includes means for releasably locking the instrument support member selectively in a plurality of different positions relative to the base, said cooperating means comprising a set screw to engage the convex surface.

4. A jig for consistently maintaining a surgical instrument in a predetermined orientation relative to a subjacent tissue on which the jig is supported, said jig comprising:

a base having a flat surface residing in a first plane for placement in facially engaged relationship with a tissue in the vicinity of where a surgical procedure is to be performed;

an instrument support member;

cooperating means on the base and instrument support member for maintaining the instrument support member in a predetermined position relative to the base and a subjacent tissue on which the jig is supported, wherein the cooperating means comprises a concave surface on one of the base and instrument support member and a convex surface on the other of the base and instrument support member, said concave and convex surfaces cooperating with each other to guide universal relative movement between the instrument support member and base; and means for releasably fixing the convex and concave surfaces in a plurality of different positions relative to each other, said convex and concave surfaces being fully spaced from the first plane, whereby the jig can be used to positively maintain a surgical instrument in a desired orientation relative to a subjacent tissue to thereby facilitate the performance of surgical procedures, wherein the cooperating means comprises means for selectively maintaining the instrument support member in a plurality of different positions relative to the base, wherein the instrument support member has a sleeve defining a passageway for the introduction of a surgical instrument to be extended into a subjacent tissue on which the jig is supported, wherein the sleeve has an axial extent and there are means on the instrument support member for releasably fixing the position of the sleeve relative to the base.

5. A jig for consistently maintaining a surgical instrument in a predetermined orientation relative to a subjacent tissue on which the jig is supported, said jig comprising:

a base having a flat surface residing in a first plane for placement in facially engaged relationship with a tissue in the vicinity of where a surgical procedure is to be performed;

an instrument support member; and cooperating means on the base and instrument support member for maintaining the instrument support member in a predetermined position relative to the base and a subjacent tissue on which the jig is supported, wherein the cooperating means comprises a concave surface on one of the base and instrument support member and a convex surface on the other of the base and instrument support member, said concave and convex surfaces cooperating with each other to guide universal relative movement between the instrument support member and base, said convex and concave surfaces being fully spaced from the first plane, whereby the jig can be used to positively maintain a surgical instrument in a desired orientation relative to a subjacent tissue to thereby facilitate the performance of surgical procedures, wherein the instrument support member has a spherical configuration defining the convex surface and the base has a socket for reception of the instrument support member and defines the concave surface, wherein the base flat surface has an annular configuration and the base includes a conical skirt converging away from the flat base surface, there being means cooperating between the conical skirt and said socket for maintaining the socket spaced from the plane of the flat surface of the base.

6. A jig for consistently maintaining a surgical instrument in a predetermined orientation relative to a subjacent tissue on which the jig is supported, said jig comprising:

a base having a flat surface, said flat surface having an effective diameter of at least 2 inches facing in a first direction for placement against a flexible tissue in the vicinity of where a surgical procedure is to be performed, there being no structure projecting from the plane of said flat surface in said first direction;

an instrument support member;

cooperating means on the base and instrument support member for maintaining the instrument support member selectively in a plurality of predetermined positions relative to the base and a subjacent tissue on which the jig is supported, said cooperating means including a cooperating ball and socket; and annular means for adhering the flat base surface to a subjacent tissue to stably support the base on a subjacent tissue, whereby the jig can be used to positively maintain a surgical instrument in a desired orientation relative to a subjacent tissue to thereby facilitate the performance of surgical procedures, wherein the base has a curved yoke and means are provided for connecting the yoke to the base for movement relative thereto, wherein the yoke has a curved slot and the instrument support member has a pin that is guided in an arcuate path in the curved yoke slot and means are provided for locking the pin in a desired position along the slot to thereby fix the relative positions of the yoke and the instrument support member.

7. The surgical instrument jig according to claim 6 wherein the yoke has an inverted U-shaped configuration.

8. A jig for consistently maintaining a surgical instrument in a predetermined orientation relative to a subjacent tissue on which the jig is supported, said jig comprising:

a base having a flat downwardly facing surface for placement facially against a tissue in the vicinity of where a surgical procedure is to be performed, there being no structure on said jig extending downwardly beyond the flat downwardly facing surface on the base;

an instrument support member; and cooperating means on the base and instrument support member for maintaining the instrument support member in a predetermined position relative to the base and a subjacent tissue on which the jig is supported, whereby the jig can be used to positively maintain a surgical instrument in a desired orientation relative to a subjacent tissue to thereby facilitate the performance of surgical procedures, wherein the cooperating means comprises means for selectively maintaining the instrument support member in a plurality of different positions relative to the base, wherein the base has a curved yoke and the cooperating means comprises a pin and slot connection on the yoke and instrument support member, wherein the yoke has a curved slot and instrument support member has a pin that is guided in an arcuate path in the curved yoke slot and means are provided for locking the pin in a desired position along the slot to thereby fix the relative positions of the yoke and the instrument support member, wherein the yoke has an inverted U-shaped configuration, wherein the base has a first wall with a flat surface for placement against a subjacent tissue and a second wall mounted to the first wall for pivoting movement relative to the first wall abut an axis that is transverse to the plane of the first flat wall surface.

9. A surgical instrument jig for consistently maintaining a surgical instrument in a predetermined orientation relative to a subjacent tissue on which the jig is supported, said jig comprising:

a base for placement against a tissue in the vicinity of where a surgical procedure is to be performed;

an instrument support member; and cooperating means on the base and instrument support member for maintaining the instrument support member in a predetermined position relative to the base and a subjacent tissue on which the jig is supported, whereby the jig can be used to positively maintain a surgical instrument in a desired orientation relative to a subjacent tissue to thereby facilitate the performance of surgical procedures, wherein the cooperating means comprises means for selectively maintaining the instrument support member in a plurality of different positions relative to the base, wherein the base has a curved yoke and the cooperating means comprises a pin and slot connection on the yoke and instrument support member, wherein the yoke has a curved slot and the instrument support member has a pin that is guided in an arcuate path in the curved yoke slot and means are provided for locking the pin in a desired position along the slot to thereby fix the relative positions of the yoke and the instrument support member, wherein the yoke has an inverted U-shaped configuration, wherein the base has a first wall with a flat surface for placement against a subjacent tissue and a second wall mounted to the first wall for pivoting movement relative to the first wall about an axis that is transverse to the plane of the first flat wall surface, wherein means are provided for selectively locking the first and second walls against relative movement.

10. A jig for consistently maintaining a surgical instrument in a predetermined orientation relative to a subjacent tissue on which the jig is supported, said jig comprising:

a base having a flat surface residing in a first plane for placement in facially engaged relationship with a tissue in the vicinity of where a surgical procedure is to be performed;

an instrument support member; and cooperating means on the base and instrument support member for maintaining the instrument support member in a predetermined position relative to the base and a subjacent tissue on which the jig is supported, wherein the cooperating means comprises a concave surface on one of the base and instrument support member and a convex surface on the other of the base and instrument support member, said concave and convex surfaces cooperating with each other to guide universal relative movement between the instrument support member and base,
said convex and concave surfaces being fully spaced from the first plane,
whereby the jig can be used to positively maintain a surgical instrument in a desired orientation relative to a subjacent tissue to thereby facilitate the performance of surgical procedures,
wherein the cooperating means comprises means for selectively maintaining the instrument support member in a plurality of different positions relative to the base,
wherein the base has a curved yoke and the cooperating means comprises a pin and slot connection on the yoke and instrument support member,
wherein the yoke has a curved slot and the instrument support member has a pin that is guided in an arcuate path in the curved yoke slot and means are provided for locking the pin in a desired position along the slot to thereby fix the relative positions of the yoke and the instrument support member,
wherein the yoke has an inverted U-shaped configuration,
wherein the base has a first wall with a flat surface for placement against a subjacent tissue and a second wall mounted to the first wall for movement relative to the first wall in a path generally parallel to the plane of the first flat wall surface.

11. A jig for allowing consistent placement of a surgical instrument in a predetermined orientation relative to a subjacent tissue on which the jig is supported, said jig comprising:
a base having a first part with a planar surface for placement facially against a tissue in the vicinity of where a surgical procedure is to be performed,
a yoke;
a second base part having means for supporting said yoke;
means interconnecting the first and second base parts for allowing pivoting of the second base part and yoke relative to the first base part about an axis that is substantially at right angles to the plane of the planar surface on the first base part;
an instrument support member on the yoke having a sleeve defining a passageway for the introduction of a surgical instrument to be extended into the tissue;
means for mounting the sleeve to the yoke for movement relative to the yoke in an arcuate path which is in a plane that is transverse to the plane of the planar surface on the first base part; and
means for maintaining the sleeve in a plurality of selected positions relative to the yoke,
whereby with the base placed against a subjacent tissue, an instrument on the instrument support member can be consistently directed through the sleeve passageway against the tissue in a consistent orientation.

12. The jig for orienting a surgical instrument according to claim 11 wherein means are provided for releasably holding the first jig base part in a fixed position relative to a subjacent tissue.

13. The jig for orienting a surgical instrument according to claim 11 wherein said instrument support member has means thereon for captively embracing a tissue through which the sleeve is extended.

14. A jig for consistently orienting a surgical instrument in a predetermined orientation relative to a subjacent tissue on which the jig is supported, said jig comprising:
a first base for placement against a tissue in the vicinity of where a surgical procedure is to be performed,
said base having a yoke;
an instrument support member on the yoke having a sleeve defining a passageway for the introduction of a surgical instrument to be extended into the tissue;
means for supporting the yoke on the base for movement relative to the base; and
means for maintaining the yoke in a plurality of selected positions relative to the base,
whereby with the base placed against a subjacent tissue, the yoke can be fixed in a preselected position, whereupon an instrument can be consistently directed through the sleeve passageway against the tissue in a consistent orientation
wherein said instrument support member has means thereon for captively embracing a tissue through which the sleeve is extended,
wherein the instrument support member sleeve has proximal and distal ends, the means for captively embracing a tissue comprises an expandable member which is positionable selectively in expanded and collapsed states at the distal end of the sleeve and a collar mounted to the sleeve for sliding movement selectively towards and away from the expandable member, whereby the sleeve with the expandable member in its collapsed state can be directed through an incision in a tissue after which the expandable member can be placed in its expanded state and the collar slid along the sleeve to captively embrace the tissue in conjunction with the expandable member in its expanded state.

15. A jig for consistently orientating a surgical instrument in a predetermined orientation relative to a subjacent tissue on which the jig is supported, said jig comprising:
a base for placement against a tissue in the vicinity of where a surgical procedure is to be performed,
said base having a yoke;
an instrument support member on the yoke having a sleeve defining a passageway for the introduction of a surgical instrument to be extended into the tissue;
means for supporting the yoke on the base for movement relative to the base; and
means for maintaining the yoke in a plurality of selected positions relative to the base,
whereby with the base placed against a subjacent tissue, the yoke can be fixed in a preselected position, whereupon an instrument can be directed through the sleeve passageway against the tissue in a consistent orientation,
wherein said yoke comprises cooperating U-shaped elements each with a body and first and second legs projecting from the body with each said leg having a free end, and means are provided for pivotably attaching the free ends of each of the legs of the yoke elements to the base so that the bodies of the U-shaped elements are pivotable selectively towards and away from each other.

16. The jig for orientating a surgical instrument according to claim 15 wherein means are provided for biasing at least one of the U-shaped elements towards the other of the U-shaped elements to thereby captively engage the instrument support member.

17. The jig for orienting a surgical instrument according to claim 16 wherein means are provided for holding the sleeve in a fixed position with respect to at least one of the U-shaped elements.

18. The jig for orienting a surgical instrument according to claim 15 wherein each U-shaped element pivots relative to the base about an axis and the pivot axes for the U-shaped elements are coincident.

19. The jig for orienting a surgical instrument according to claim 15 wherein each U-shaped element pivots relative to the base about an axis and the pivot axes for the U-shaped elements are substantially parallel to and spaced from each other.

20. A jig for consistently maintaining a surgical instrument in a predetermined orientation relative to a subjacent tissue on which the jig is supported, said jig comprising:
    a base having a flat surface, said flat surface having an effective diameter of at least 2 inches facing in a first direction for placement against a flexible tissue in the vicinity of where a surgical procedure is to be performed,
    there being no structure projecting from the plane of said flat surface in said first direction;
    an instrument support member;
    cooperating means on the base and instrument support member for maintaining the instrument support member selectively in a plurality of predetermined positions relative to the base and a subjacent tissue on which the jig is supported,
    said cooperating means including a cooperating ball and socket; and
    annular means for adhering the flat base surface to a subjacent tissue to stably support the base on a subjacent tissue,
    whereby the jig can be used to positively maintain a surgical instrument in a desired orientation relative to a subjacent tissue to thereby facilitate the performance of surgical procedures.

21. The surgical instrument jig according to claim 20 wherein the base has a curved yoke and means are provided for connecting the yoke to the base for movement relative thereto.

* * * * *